(12) United States Patent
Aranibar et al.

(10) Patent No.: US 9,839,452 B1
(45) Date of Patent: Dec. 12, 2017

(54) SPINAL REPAIR IMPLANTS AND RELATED METHODS

(71) Applicants: Roberto J. Aranibar, San Antonio, TX (US); Roberto G. Aranibar, San Antonio, TX (US)

(72) Inventors: Roberto J. Aranibar, San Antonio, TX (US); Roberto G. Aranibar, San Antonio, TX (US)

(*) Notice: Subject to any disclaimer, the term of this patent is extended or adjusted under 35 U.S.C. 154(b) by 0 days.

(21) Appl. No.: 15/599,238

(22) Filed: May 18, 2017

Related U.S. Application Data (63) Continuation of application No. 15/353,379, filed on Nov. 16, 2016, now Pat. No. 9,687,280, which is a continuation of application No. 14/826,052, filed on Aug. 13, 2015, now Pat. No. 9,526,533.

(60) Provisional application No. 62/049,695, filed on Sep. 12, 2014, provisional application No. 62/049,707, filed on Sep. 12, 2014, provisional application No. 62/068,793, filed on Oct. 27, 2014.

(51) Int. Cl.
*A61B 17/70* (2006.01)

(52) U.S. Cl.
CPC ...... *A61B 17/7067* (2013.01); *A61B 17/7032* (2013.01); *A61B 17/7035* (2013.01); *A61B 17/7043* (2013.01); *A61B 17/7055* (2013.01); *A61B 17/7058* (2013.01)

(58) Field of Classification Search
CPC ............ A61B 17/7058; A61B 17/7059; A61B 17/7071; A61B 17/8004; A61B 17/8009; A61B 17/7067
See application file for complete search history.

(56) References Cited

U.S. PATENT DOCUMENTS

| | | | | |
|---|---|---|---|---|
| 4,429,690 A | * | 2/1984 | Angelino-Pievani | A61B 17/80 606/280 |
| 5,437,672 A | * | 8/1995 | Alleyne | A61B 17/00 606/279 |
| 5,611,354 A | * | 3/1997 | Alleyne | A61B 17/00 128/846 |
| 5,743,913 A | * | 4/1998 | Wellisz | A61B 17/8061 606/285 |
| 5,766,254 A | * | 6/1998 | Gelbard | A61B 17/7032 606/250 |

(Continued)

OTHER PUBLICATIONS

Panchai, Ripul R et al., "Cervical Spinous Process Reconstruction", J. Neurosurg. Spine 20: Jan. 18-21, 2014 (4 pages).

*Primary Examiner* — Ellen C Hammond
*Assistant Examiner* — Stuart S Bray
(74) *Attorney, Agent, or Firm* — Pizarro Allen PC (57) ABSTRACT

A spinal implant may include a frame having a plurality of attachment portions each configured to be received by a head of a bone anchor, a cover extending between at least two portions of the frame, and a plurality of spaces between the cover and the frame each of which is configured to accommodate the head of a bone anchor. Some embodiments may include a frame having a plurality of segments connected by joints. Some embodiments may have two or more covers in sliding engagement with one another and a plurality of attachments depending from transverse members, wherein each of the plurality of attachments includes a recess configured for receiving a mounting rod. Related methods are also disclosed.

13 Claims, 12 Drawing Sheets

(56) References Cited

U.S. PATENT DOCUMENTS

| | | |
|---|---|---|
| 6,454,767 B2 | 9/2002 | Alleyne |
| 8,663,295 B2 | 3/2014 | Butler et al. |
| 9,023,085 B2 * | 5/2015 | Strippgen .................. A61F 2/28 606/280 |
| 2002/0123750 A1 * | 9/2002 | Eisermann ............. A61B 17/68 606/285 |
| 2003/0078588 A1 | 4/2003 | Alleyne |
| 2005/0071006 A1 * | 3/2005 | Kirschman ........ A61B 17/7059 623/17.11 |
| 2005/0149021 A1 * | 7/2005 | Tozzi ................. A61B 17/7058 606/280 |
| 2005/0149032 A1 * | 7/2005 | Vaughen ............ A61B 17/8085 606/77 |
| 2006/0264948 A1 * | 11/2006 | Williams ............... A61B 17/70 606/71 |
| 2007/0078461 A1 * | 4/2007 | Shluzas .................. A61B 17/70 606/279 |
| 2007/0100341 A1 * | 5/2007 | Reglos ............... A61B 17/7004 606/86 A |
| 2008/0021462 A1 * | 1/2008 | Trieu ...................... A61L 27/34 623/17.11 |
| 2009/0326592 A1 * | 12/2009 | Butler ................ A61B 17/7058 606/286 |
| 2010/0152575 A1 * | 6/2010 | Henderson ......... A61B 17/7055 600/425 |
| 2010/0174315 A1 * | 7/2010 | Scodary ............. A61B 17/7043 606/248 |
| 2010/0179597 A1 * | 7/2010 | Henderson ......... A61B 17/7055 606/264 |
| 2010/0256765 A1 * | 10/2010 | Butler ................ A61B 17/0642 623/17.16 |
| 2010/0268278 A1 * | 10/2010 | Foley ................. A61B 17/7059 606/263 |
| 2011/0270397 A1 * | 11/2011 | Mac-Thiong ...... A61B 17/7071 623/17.11 |
| 2011/0313323 A1 * | 12/2011 | Henderson ......... A61B 17/7055 600/594 |
| 2012/0150230 A1 * | 6/2012 | Felix .................. A61B 17/7052 606/250 |
| 2012/0316649 A1 * | 12/2012 | Johnston ................. A61F 2/447 623/17.16 |
| 2014/0005723 A1 * | 1/2014 | Shah .................. A61B 17/7059 606/248 |
| 2014/0128916 A1 | 5/2014 | Williams |

* cited by examiner

SPINAL REPAIR IMPLANTS AND RELATED METHODS

CROSS-REFERENCE TO RELATED APPLICATIONS

This application is a continuation of U.S. patent application Ser. No. 15/353,379 filed Nov. 16, 2016, which is a continuation of U.S. patent application Ser. No. 14/826,052 filed Aug. 13, 2015, now U.S. Pat. No. 9,526,533 issued Dec. 27, 2016, which claims priority to U.S. Provisional Patent Application No. 62/049,695 filed Sep. 12, 2014; U.S. Provisional Patent Application No. 62/049,707 filed Sep. 12, 2014; and U.S. Provisional Patent Application No. 62/068,793 filed Oct. 27, 2014; the disclosure of each of which is incorporated herein by reference.

COPYRIGHT NOTICE

This application contains material that is subject to copyright protection. Such material may be reproduced exactly as it appears in Patent and Trademark Office patent files or records. The copyright owner otherwise reserves all rights to such material.

FIELD

This application relates generally to the field of spinal implants.

BACKGROUND

In the field of spinal implants, structural constructs that include bone screws, rods, and transverse connectors are routinely implanted during spinal laminectomy procedures in order to stabilize motion between adjacent vertebrae and maintain decompression of the spinal cord and nerve roots. While effective in this respect, such constructs leave the spinal dura exposed and unprotected after the resection of posterior spinal elements that make up the vertebral arches (e.g., particularly the laminae and spinous processes). Moreover, such constructs do not prevent post-operative scar tissue adhesion onto the dura or effectively address situations in which the paraspinal musculature and ligaments atrophy due to their surgical disturbance and compromised vascularity. Paraspinal tissue atrophy can result in outwardly visible and unsightly concave defects along the posterior aspect of the spine, the implications of which go beyond cosmetic factors only. Specifically, the development of concavities along the posterior spine can lead to a dangerously superficial position of the exposed and unprotected dura and sensitive underlying spinal tissue. This superficial position of the dura can make a patient susceptible to pain from even the most trivial palpation on the outside of the body near the exposed region of the dura. More importantly, this position makes non-regenerative central nervous system tissue more vulnerable to injury or serious trauma. It would be a significant advancement in the art to provide a spinal implant that would stabilize the spine while simultaneously restoring the protective function of the vertebral arches, thereby preventing or minimizing the chances of all of the aforementioned risks and complications associated with spinal laminectomy procedures.

SUMMARY

In some embodiments, a spinal implant may include a frame having a plurality of attachment portions each configured to be received by a head of a bone anchor, a cover extending between at least two portions of the frame, and a plurality of spaces between the cover and the frame each of which is configured to accommodate the head of a bone anchor.

In some embodiments, a spinal implant may include a frame having a plurality of segments connected by joints, the frame having a plurality of attachment portions each configured to be received by a head of a bone anchor; at least one cover connected to the frame; and a plurality of spaces between the at least one cover and the frame, each of which is configured to accommodate the head of a bone anchor.

In some embodiments, a spinal implant may include a first transverse member; a first cover depending from the first transverse member; a second transverse member; a second cover depending from the second transverse member; the first and second covers being in sliding engagement with one another; and a plurality of attachments depending from each of the first and second transverse members, wherein each of the plurality of attachments comprises a recess configured for receiving a mounting rod.

In some embodiments, a method of repairing a spine may include installing a plurality of bone anchors in the spine, each of the plurality of bone anchors having a head with a recess; positioning an implant such that attachment portions of a frame of the implant are respectively disposed in the recesses of the heads of the bone anchors; and fastening the respective heads of the bone anchors to the attachment portions of the frame; wherein the implant has a cover extending between at least two portions of the frame configured for protecting a portion of the spine and a plurality of spaces between the cover and the frame each of which is configured to accommodate the head of one of the bone anchors. In some embodiments, the frame may be a segmented frame including a plurality of frame members joined by one or more suitable joints.

In some embodiments, a method of repairing a spine may include installing a plurality of bone anchors in the spine, each of the plurality of bone anchors having a head with a recess; installing a plurality of rods in the recesses of the heads of the bone anchors; fastening the plurality of rods to the heads of the bone anchors; and fastening an implant to the plurality of rods using a plurality of set screws; wherein the implant has at least one cover extending between spaced apart transverse members and configured for protecting a portion of the spine; and wherein the transverse members have a plurality of attachments each of which has a recess configured for receiving one of the plurality of rods. In some embodiments, the at least one cover may include a plurality of covers slidably engaged with each other.

DETAILED DESCRIPTION

As used herein, the following terms should be understood to have the indicated meanings:

When an item is introduced by "a" or "an," it should be understood to mean one or more of that item.

"Comprises" means includes but is not limited to.

"Comprising" means including but not limited to.

"Having" means including but not limited to.

As illustrated in the drawings, this application is generally directed to spine implants designed to stabilize motion within the spine while simultaneously protecting the posterior aspect of the spinal dura and underlying tissues from risks and complications following spinal surgeries, such as laminectomies, for example, involving surgical resection of the posterior spinal elements, including the laminae and spinous processes. Such implants may be placed in the cervical, thoracic, and/or lumbar regions of the spine, with some embodiments extending as far as the occipital region of the skull. Some of the primary purposes of such implants are (1) to restore the structural functionality of the vertebral arches, thereby (a) protecting surgically exposed regions of the spinal dura and (b) eliminating pain and risks associated with post-operative developments of concave defects over the posterior spine due to atrophy of the paraspinal musculature and ligaments caused by surgical detachment of these tissues and compromise of their vascularity, (2) to prevent adhesion of scar tissue to the dura, and (3) to stabilize motion within the spine by eliminating or providing a controlled range of relative motion between adjacent vertebrae. Spinal devices as described herein may be used to fix or control relative motion between adjacent vertebrae in order to maintain decompression of the spinal cord and nerve roots, protect exposed regions of the spinal dura, and preserve the general shape and protective function of the vertebral arches.

In some embodiments, such an implant may include a substantially flat or arched frame and a fenestrated cover that extends between the superior-most and inferior-most transverse portions of the frame. The fenestrations in the cover may be of any shape and size. In some embodiments, the cover may be made of a wire mesh material that is compressible along one or more axes. If arched, the contour of the frame may exhibit any degree and type of curvature. The superior-most portion of the frame may or may not include a notch, which may serve to better accommodate the spinous process of an adjacent superior vertebrae. Such implants may be affixed to the posterior aspect of the spine by securing the frame to the heads of bone anchors, which are inserted into or affixed to the pedicles, lateral masses, or other bony structures of the vertebrae. Securing the frame to the heads of bone anchors may be accomplished by the use of threaded or non-threaded caps, clamps, pins, crimps, interlocking shapes, or any other suitable mechanism. In some embodiments, the frame may comprise a plurality of rod members that are joined together by springs, which may attach to the frame by any suitable means, such as inserting the rod members into the springs, inserting the springs into hollow rod members, or wrapping the spring ends about pins depending from the frame, for example. The springs may be of any suitable type, such as tension, compression, or torsion, for example. Such embodiments may provide a degree of flexibility and preserve a limited range of relative motion between the vertebrae, while still fulfilling some or all of the other purposes of the implant described in the preceding paragraph. Some embodiments may include rod-like extensions protruding from the frame of the apparatus toward the occipital region of the skull. The rod-like extensions may be bent and secured within the heads of occipital anchors, which may or may not be part of an occipital plate, in order to provide cranio-cervical stability in certain applications.

The physical dimensions (e.g., width, length, height, frame diameter, and cover thicknesses) of such an implant may vary based on several factors, including the region and anatomy of the spine in which it is implanted. Despite this variance, the typical ranges of physical dimensions of the implant may be approximated as shown in Table 1:

TABLE 1

| Dimension | Minimum (mm) | Maximum (mm) |
| --- | --- | --- |
| Width | 10 | 100 |
| Length | 10 | 200 |
| Height | 5 | 50 |
| Frame Diameter | 2 | 7 |
| Cover Thickness | 0.25 | 3 |

Of course, any suitable dimensions may be used, depending on the particular application.

Implants as described herein may be comprised of one or more biocompatible materials, including but not limited to titanium, aluminum, vanadium, cobalt, chrome, molybdenum, nickel, and/or various alloys of each (e.g., Ti6Al4V, cobalt chromium, and nitinol), for example, or combinations thereof. The material or combination of materials selected for an implant may influence whether the implant eliminates or provides a controlled range of relative motion between adjacent vertebrae (i.e., whether it provides fixed or dynamic stabilization). For example, the use of a relatively flexible or superelastic material such as nitinol may result in the implant allowing some degree of relative motion between adjacent vertebrae, while the use of a relatively stiff material such as Ti6Al4V or cobalt chromium may substantially prevent such motion. In some instances, a stiffer material may be implanted with bone graft in order to induce long-term bony fusion (i.e., providing fixed stabilization), whereas a more flexible material may be implanted without graft in order to preserve some degree of motion (i.e., providing dynamic stabilization). Nevertheless, if comprised of a stiffer material, the material may be pliable via the use of instruments employing even stiffer materials, such as stainless steel, for example, which may enable surgeons to precisely bend and conform the implant to the unique shape and contour required by any patient or spinal region. In some embodiments, the materials used in the implant may also allow it to be safely introduced into the electromagnetic field of a magnetic resonance imaging (MRI) scanner or other diagnostic machine.

Figure 1:
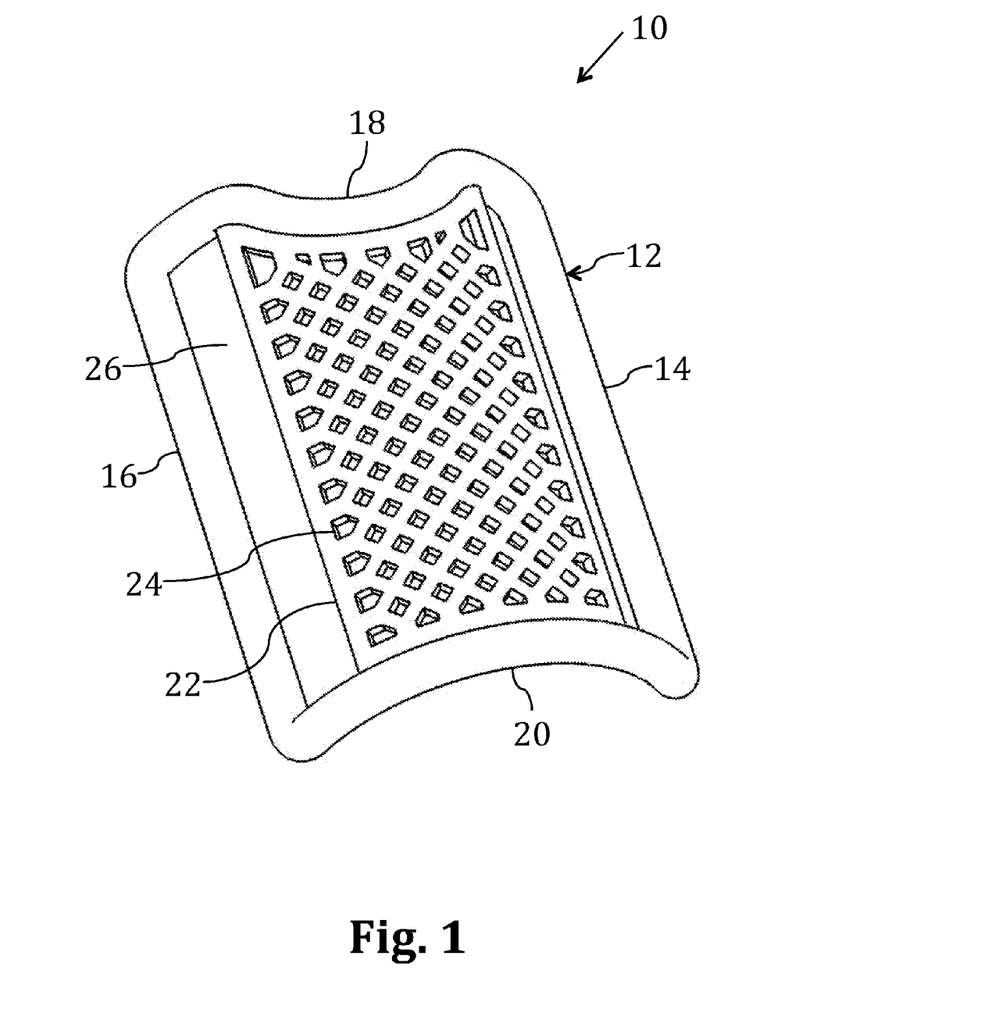
FIG. 1 is a perspective view of a spinal implant.
Figure 2:
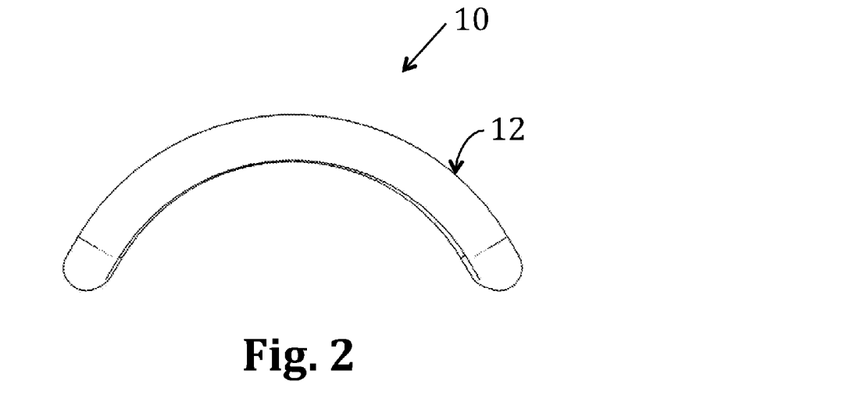
FIG. 2 is a front elevational view of the spinal implant of FIG. 1.
Figure 3:
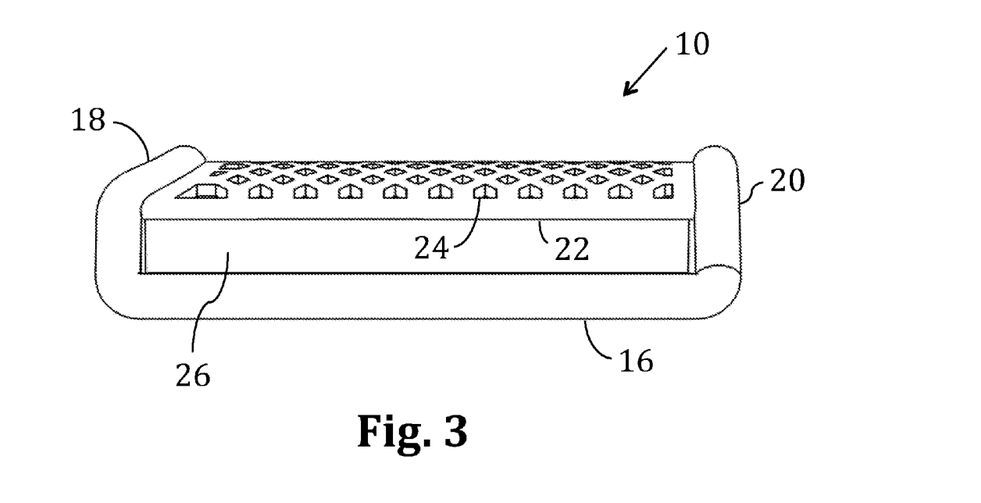
FIG. 3 is a side elevational view of the spinal implant of FIG. 1.

As shown in FIGS. 1-3, in some embodiments, a spinal implant 10 may have a frame 12 including longitudinal portions 14, 16 and transverse portions 18, 20 that form a closed structural circuit. Although longitudinal portions 14, 16 and transverse portions 18, 20 of frame 12 are illustrated as rod portions having a generally circular cross-section, such portions may have any suitable form and cross-sectional shape. Transverse portions 18, 20 may or may not be oriented perpendicular to longitudinal portions 14, 16. Although frame 12 is illustrated as being one integral piece, frame 12 may be formed from separate pieces joined by suitable fasteners, such as weldments, screws, clamps, or the like. Implant 10 may have a cover 22 extending between transverse portions 18 and 20 to help protect posterior aspects of the spinal dura after surgical resection of posterior spinal elements, including the laminae and spinous processes. In some embodiments, cover 22 may have one or more fenestrations 24 to allow fluid seepage through implant 10, thereby preventing fluid buildup beneath implant 10 and elevated pressure on the dura. Fenestrations 24 may be of any suitable size, shape, number, and placement. Implant 10 may also have one or more spaces 26 between longitudinal portions 14, 16 and cover 22 to help facilitate attachment to bone screws or other anchors as described further below.

Figure 4:
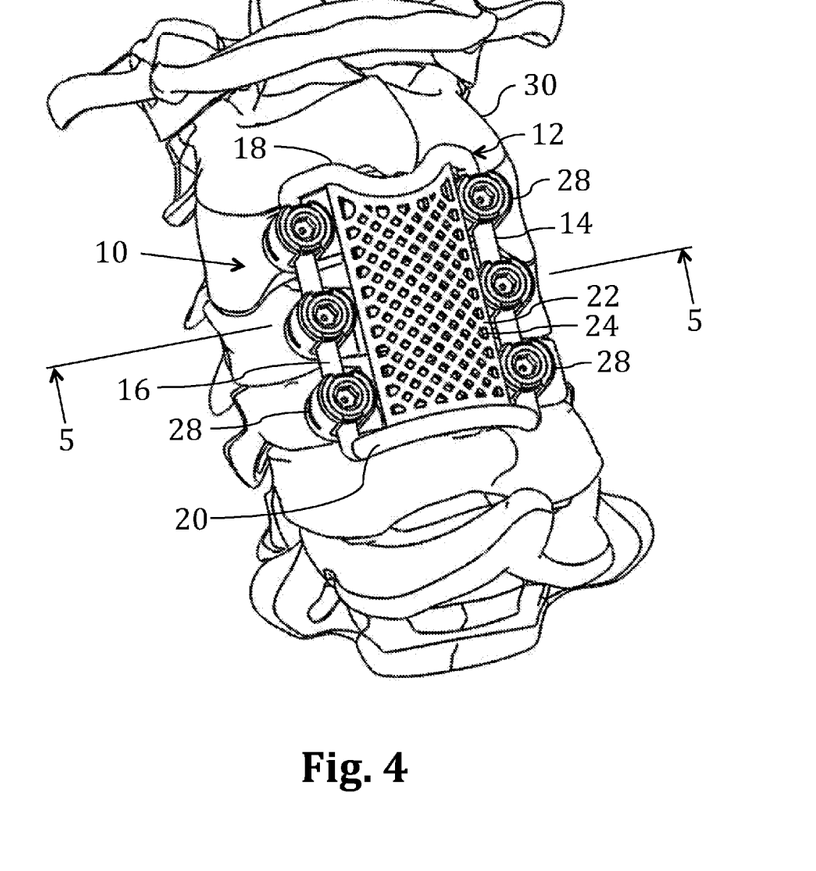
FIG. 4 is a perspective view of the spinal implant of FIG. 1 installed on a spine post-laminectomy at spinal levels C3 through C5.
Figure 5:
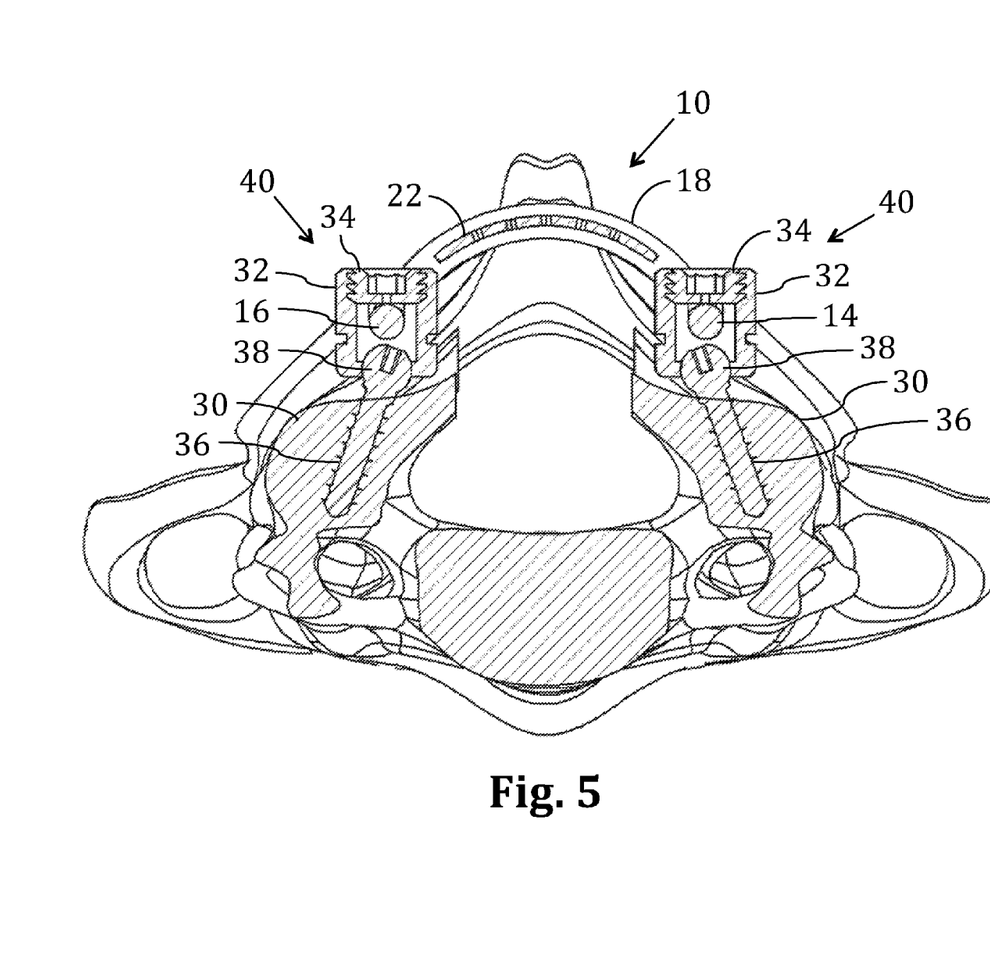
FIG. 5 is a cross-sectional view of the spinal implant of FIG. 1 taken in the direction of arrows 5-5 as shown in FIG. 4.

Referring to FIGS. 4 & 5, spinal implant 10 may be fastened to a portion of a spine 30 at a plurality of bone anchor attachments 28 by inserting longitudinal portions 14, 16 of frame 12 into recesses of heads 32 of bone screws 40 and tightening threaded caps 34 into corresponding threaded receptacles of heads 32, thereby fixing longitudinal portions 14, 16 with respect to each bone screw 40. Each bone screw 40 may have a threaded shaft 36 that may be screwed into a bone of the spine 30 and a slotted ball head 38 seated in a recess of head 32. Transverse portions 18 and 20 of frame 12 and cover 22 may be curved or otherwise configured to generally conform to the desired arched shape of the posterior spine and ensure adequate clearance between the spinal dura and skin post-operatively. In lieu of or in addition to bone screws 40, any suitable bone anchors (such as hooks configured to hook onto a bone, or pins configured to press into a hole or recess of a bone, for example) may be used to install implant 10 and the other implants described herein. In some embodiments, in lieu of or in addition to threaded caps 34 being screwed into corresponding threaded receptacles of heads 32, the bone anchors may be secured to the longitudinal portions 14, 16 of frame 12 by any other suitable means, such as clamps, pins, crimps, or interlocking shapes, for example.

Figure 6:
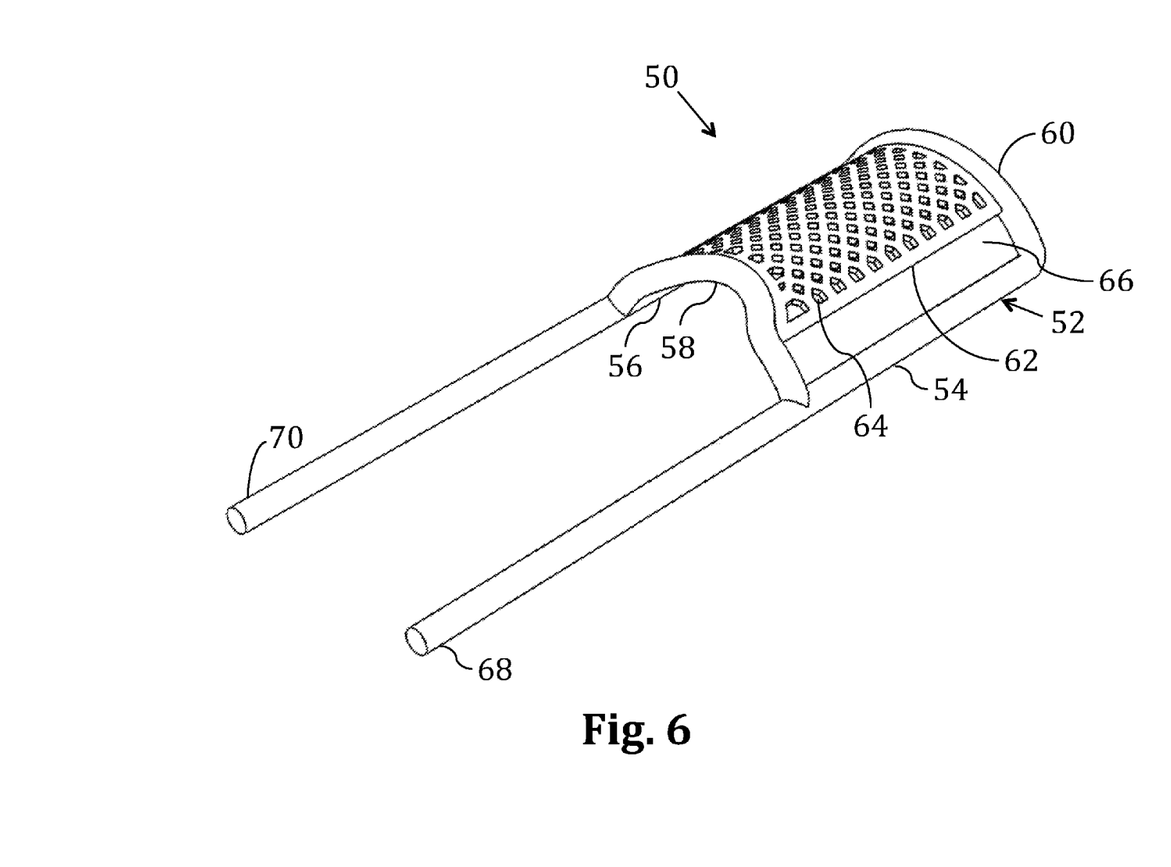
FIG. 6 is a perspective view of an occiput-compatible embodiment of a spinal implant.
Figure 7:
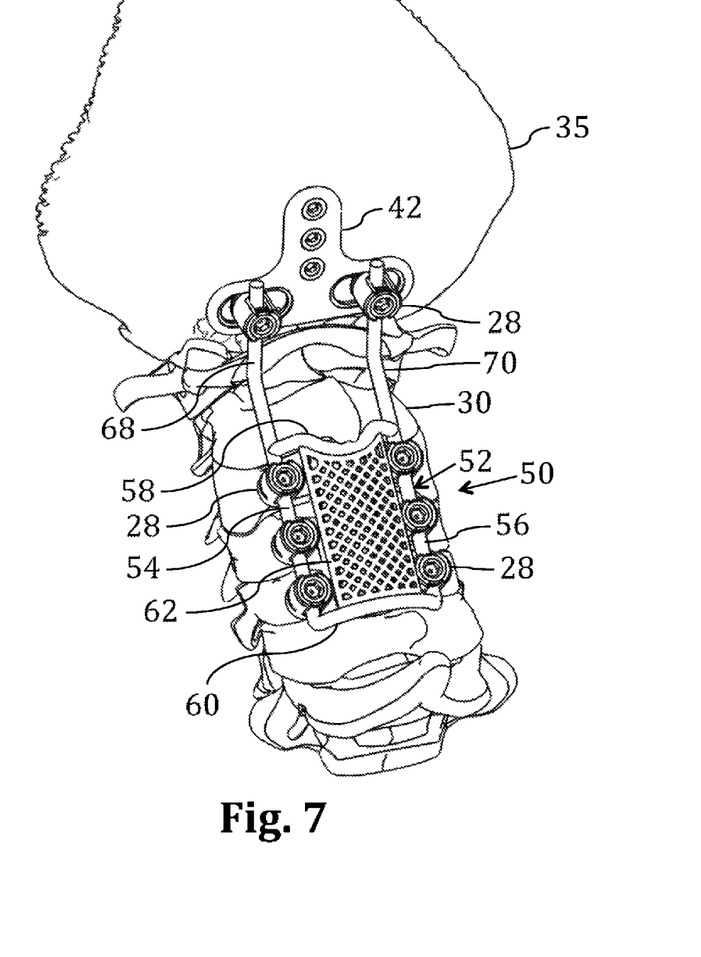
FIG. 7 is a perspective view of the spinal implant of FIG. 6 installed on a spine post-laminectomy at spinal levels C3 through C5.

As shown in FIGS. 6 & 7, in some embodiments, a spinal implant 50 may be specially configured with extensions 68, 70 that protrude from the frame 52 toward the occipital region of the skull 35. For example, in some embodiments, extensions 68, 70 may protrude approximately 20-150 mm or other suitable length beyond transverse portion 58 of frame 52. This is an optional enhancement of implant 10 described above that allows surgeons to treat patients who require stabilization of the spine up to the occiput while reaping the same benefits of implant 10 described above. This enhancement may be used to address instances in which, for clinical reasons, a surgeon desires that the implant extend to the occiput. Similar to implant 10 described above, implant 50 may have a frame 52 having longitudinal portions 54, 56 and transverse portions 58, 60. A cover 62 may extend between transverse portions 58 and 60, and cover 62 may have one or more fenestrations 64. Implant 50 may have one or more spaces 66 between longitudinal portions 54, 56 and cover 62 to help facilitate attachment of longitudinal portions 54, 56 to bone anchors as described above for implant 10. In some embodiments, extensions 68, 70 may be bent to a desired degree determined by the angle between the cervical spine and occiput for the particular patient. Extensions 68, 70 may then be secured to occipital bone anchor attachments 28, which may or may not be part of an occipital plate 42, similar to longitudinal portions 54, 56.

Figure 8:
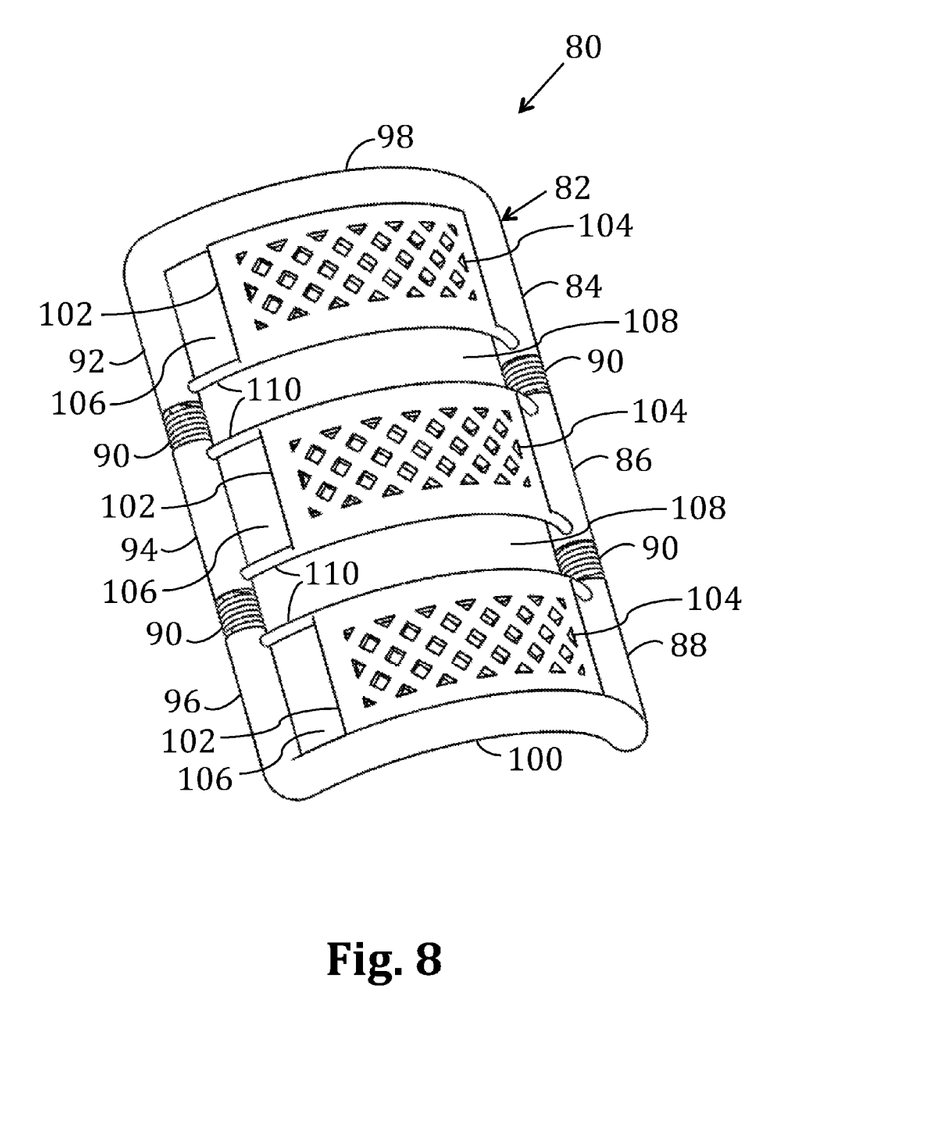
FIG. 8 is a perspective view of another embodiment of a spinal implant.
Figure 12:
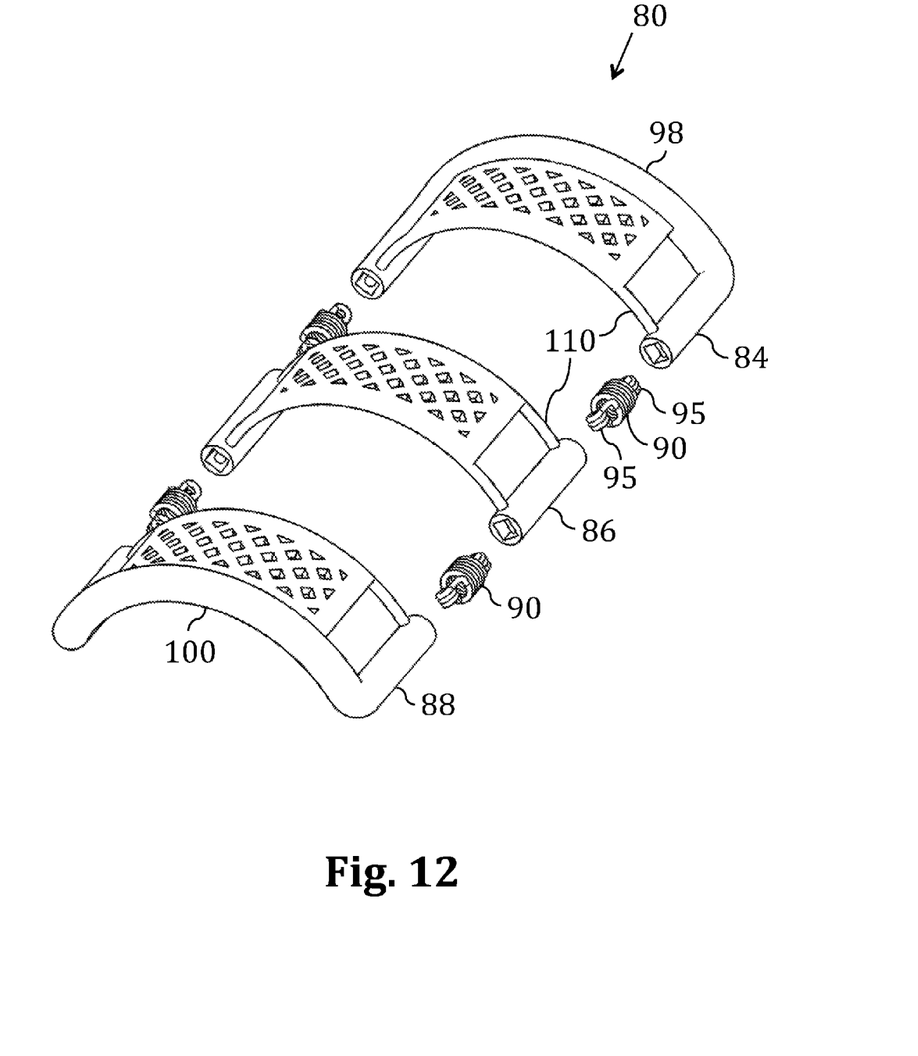
FIG. 12 is an exploded perspective view of the spinal implant of FIG. 8.

Referring to FIG. 8, in some embodiments, a spinal implant 80 may have a segmented frame 82 including a plurality of frame members joined by one or more suitable elastic or inelastic joints to provide a desired range of motion for implant 80. An added benefit of this variation is that it may protect the spinal dura while preserving a limited range of relative motion between adjacent vertebrae, thereby more closely resembling the natural physiology of the spine. For example, frame 82 may have a first member 84 joined to a second member 86 with a joint 90, and second member 86 may be joined to a third member 88 with a joint 90. Similarly, frame 82 may have a fourth member 92 joined to a fifth member 94 with a joint 90, and fifth member 94 may be joined to a sixth member 96 with a joint 90. In some embodiments, joints 90 may be springs, for example, which may be attached to adjacent members of frame 82 by any suitable means, such as by inserting the attachment members (e.g., members 84, 86) into the springs, inserting the springs into hollow portions of the attachment members, wrapping the spring ends about pins depending from the frame, applying adhesive, or welding, for example. Referring to FIG. 12, in some embodiments, joints 90 may include springs having an attachment coil 95 at each end through which a pin (such as a portion of lateral member 110 extending into a hollow portion of member 84 or 86, for example) may be inserted. The springs may be of any suitable type, such as tension, compression, or torsion, for example, with hook, loop, or coil attachment ends. Such springs may be made of wire having a diameter of approximately 1-3 mm, for example, or other suitable dimension. Of course, any suitable joint may be employed for joints 90 (e.g., ball joints, pin joints, or the like), which may be the same or different, depending on the particular application. Joints 90 may provide a limited range of relative motion along any axis between adjacent vertebrae. Members 84 and 92 may be connected by a transverse member 98, and members 88 and 96 may be connected by a transverse member 100. Although members 98 and 100 are illustrated as being continuous rather than segmented, members 98 and 100 may be segmented as well. Implant 80 may have one or more covers 102 depending from the various members of frame 82, and covers 102 may have one or more fenestrations 104. For example, covers 102 may be connected to members of frame 82 by lateral members 110. In some embodiments, each cover 102 may be connected to members of only one frame segment (e.g., a superior end segment comprised of members 84, 92, 98, or a middle segment comprised of members 86, 94, or an inferior end segment comprised of members 88, 96, 100), or a cover 102 may be connected to more than one frame segment. The number of segments and members in frame 82 and the number of joints 90 in implant 80 may vary, depending on the number of spinal segments that implant 80 is used to treat. The connections between covers 102 and frame 82 may be fixed or may have one or more degrees of freedom (e.g., pin connection, ball joint, spring, or the like). One or more spaces 106 may be provided to accommodate bone anchor connections as described above for implant 10, and one or more spaces 108 may be provided between covers 102 to accommodate movement of joints 90.

Alternatively or additionally, a desired range of motion for an implant as described herein may be provided by making one or more selected portions of the frame more flexible than other portions of the frame. For example, in some embodiments, instead of placing a joint at a particular location on a segmented frame, that portion of the frame may be made of a more flexible material than the adjacent portions, or that portion of the frame may be slimmer than the adjacent portions, or that portion of the frame may have a lower moment of inertia about a selected axis than the adjacent portions, or a combination thereof. By configuring an implant with one or more selected portions having more flexibility with respect to selected load conditions (e.g., shear, bending, torsion, or a combination thereof) than other portions of the implant, an implant may be tailored to provide a desired range of motion between targeted vertebrae or for a selected range of vertebrae of a patient.

Alternatively or additionally, a desired range of motion and/or adjustability for an implant as described herein may be provided by hinging the frame and one or more covers along a desired axis (e.g., a cranio-caudal axis). For example, an implant may include two symmetric or asymmetric halves each having an open or closed frame and a cover attached to the frame, wherein the two halves are joined by one or more hinges. The one or more hinges may join the respective frames, the respective covers, or both the respective frames and the respective covers.

Figure 9:
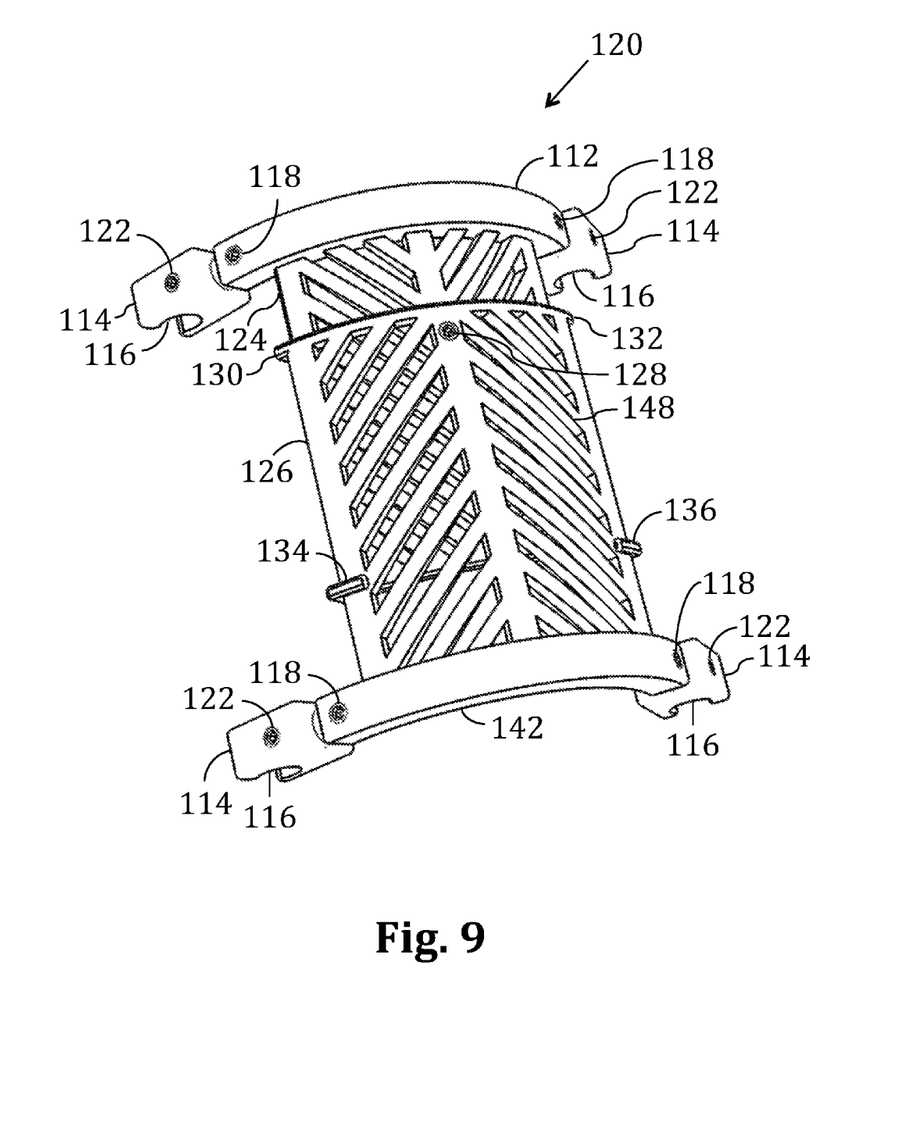
FIG. 9 is a perspective view of still another embodiment of a spinal implant.
Figure 10:
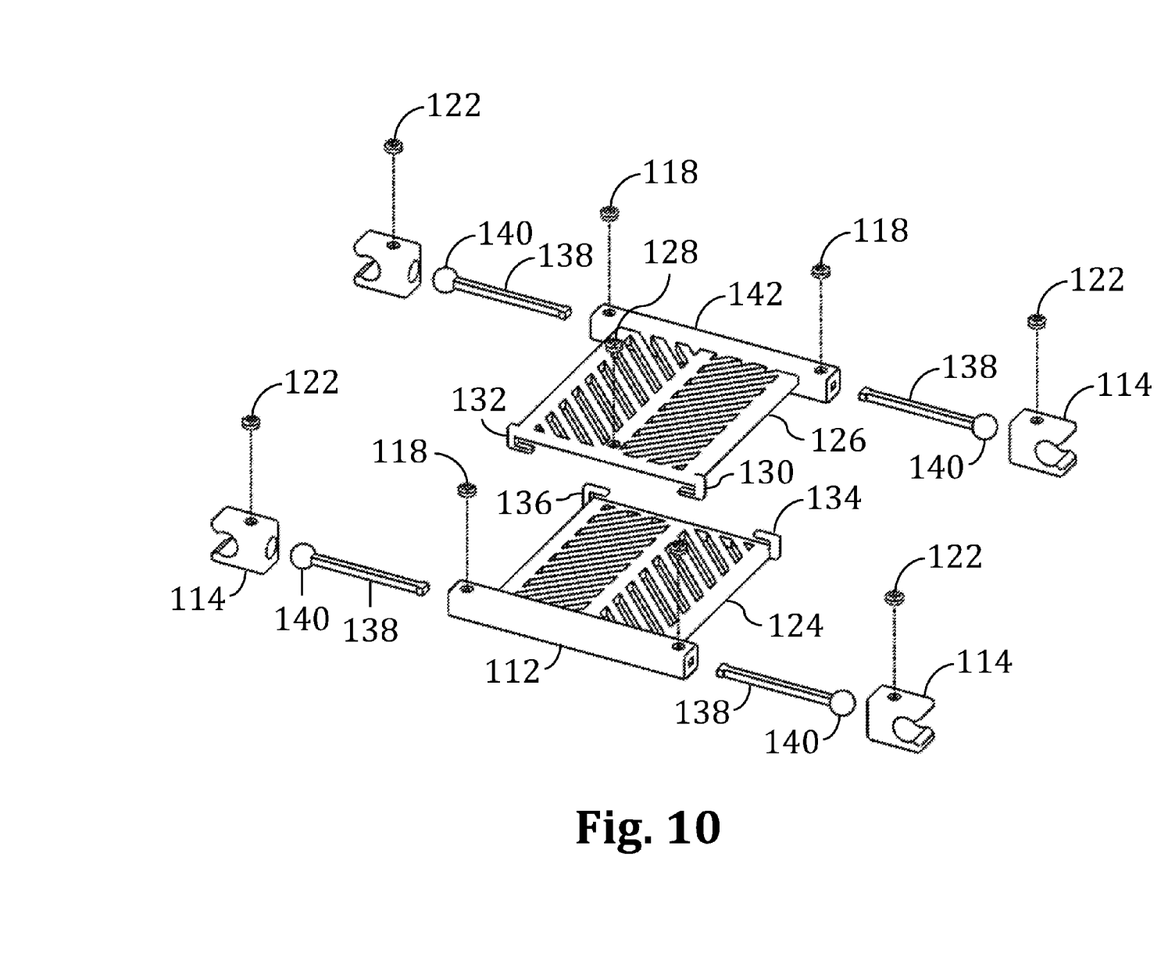
FIG. 10 is an exploded perspective view of the spinal implant of FIG. 9.

Referring to FIGS. 9 & 10, in some embodiments, a spinal implant 120 may include two or more cover elements in overlying sliding engagement with one another. This variation offers a permeable protective covering and is expandable over a range of lengths along the cranio-caudal axis. For example, implant 120 may have a first cover 124 depending from a first transverse member 112 (e.g., oriented along a medio-lateral axis) and a second cover 126 depending from a second transverse member 142. Each of cover 124 and cover 126 may have one or more fenestrations, such as slots 148, for example. Transverse members 112 and 142 may have recesses for receiving shafts 138 having balls 140 configured for rotationally seating in respective attachments 114. Each attachment 114 may have a recess 116 configured for receiving a mounting rod as described further below. A set screw 122 may be provided in each attachment 114 for fastening attachment 114 to a mounting rod as described below and for fixing the rotational position of attachment 114 relative to the ball 140 of receiving shaft 138, and a set screw 118 may be provided to fix each shaft 138 with respect to transverse member 112 or 142, respectively. Persons of ordinary skill in the art will appreciate that such an arrangement of shafts 138 and attachments 114 may provide a significant degree of lateral adjustment for implant 120. Similarly, longitudinal adjustment may be provided by a sliding arrangement of cover 124 and cover 126, which may be held in general alignment with each other by guides 130, 132, 134, and 136. Such guides or guide pairs may be of any suitable configuration, and in some embodiments such guides may be unitary guides that may span an entire width, length, or other dimension of implant 120. Once covers 124 and 126 are placed in a desired position with respect to each other, they may be fixed in that position by a set screw 128. Of course, in some embodiments, the transverse and longitudinal directions may be switched, with implant 120 oriented such that members 112 and 142 are substantially parallel to the spine and covers 124, 126 slide in a medio-lateral direction transverse to the spine. Members 112, 142 and covers 124, 126 may be provided with appropriate curvature for such an orientation. Moreover, in some embodiments, rather than having two or more cover elements in sliding engagement with one another, implant 120 may have a single cover extending between transverse members 112 and 142.

Figure 11:
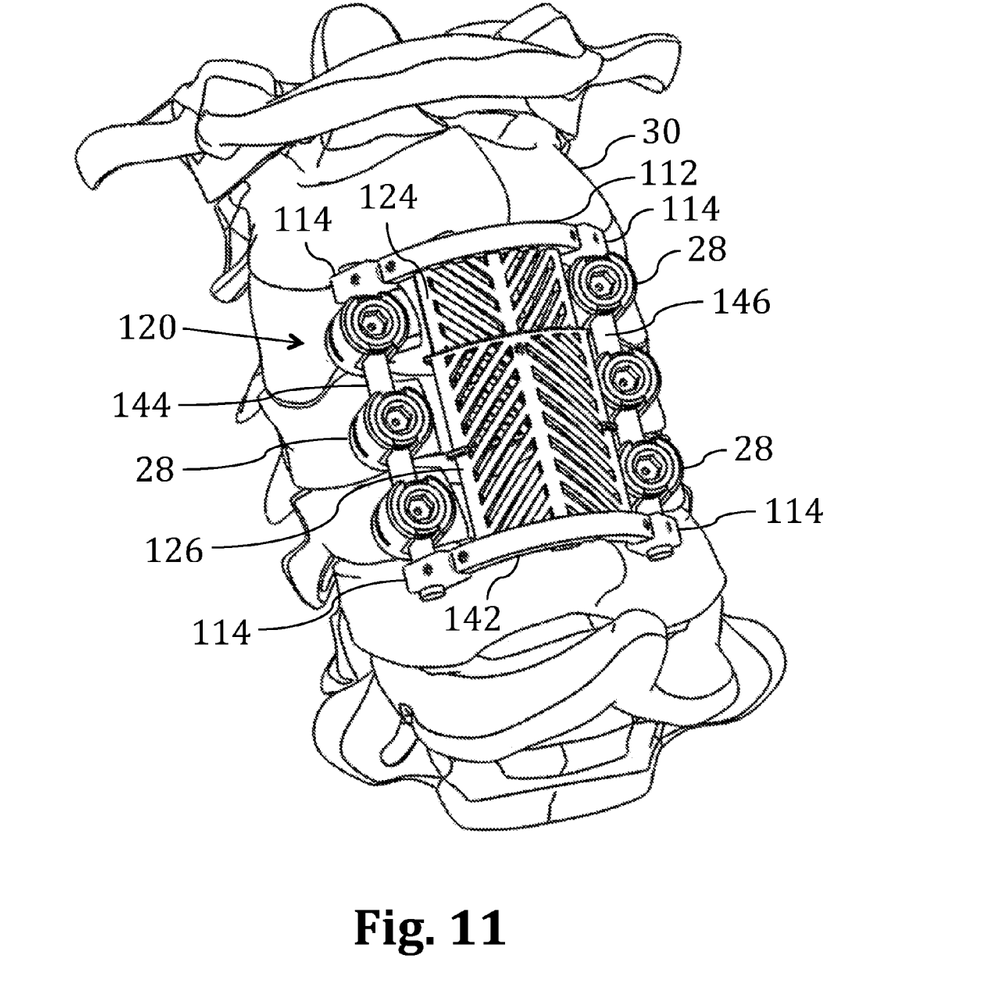
FIG. 11 is a perspective view of the spinal implant of FIG. 9 installed on a spine post-laminectomy at spinal levels C3 through C5.

As shown in FIG. 11, implant 120 may be attached to a spine 30 with a plurality of bone anchor attachments 28 similar to implant 10 described above, except that rather than frame 12 being captured between head 32 and cap 34 of each bone screw 40, rods 144 and 146 are so captured. Each of rods 144 and 146 may also be disposed in a respective recess 116 (see FIG. 9) of each attachment 114 and fastened with a set screw 122 in each attachment 114, thereby securing implant 120 in place on spine 30. Although transverse members 112 and 142 and covers 124, 126 are illustrated in FIG. 10 as generally flat, persons of ordinary skill in the art will appreciate that transverse members 112 and 142 and covers 124, 126 may be curved or otherwise shaped as illustrated in FIGS. 9 & 11 (including compound curvature, if needed) in order to provide the desired shaping for the posterior aspect of spine 30 (e.g., a shape substantially the same as a spinous process shape). As with the other embodiments described above, such shaping may be provided in the manufacture of implant 120 or by a physician or other medical personnel at the time of surgery.

Figure 1A:
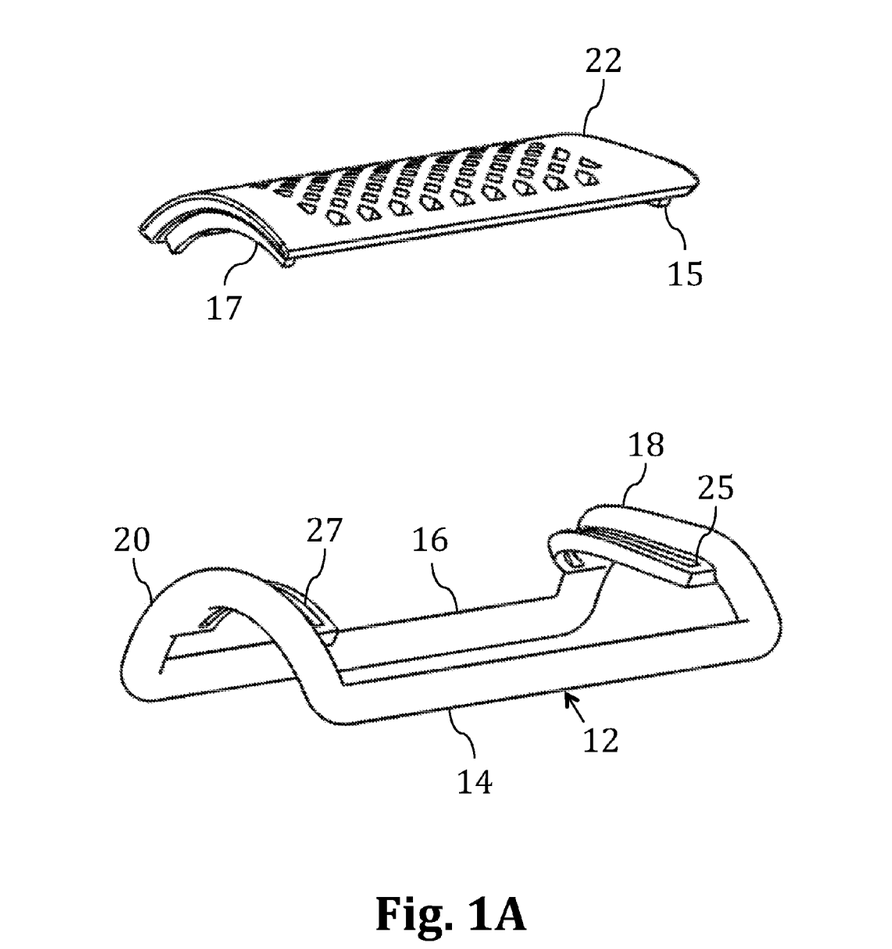
FIG. 1A is an exploded perspective view of the spinal implant of FIG. 1.

In some embodiments, an implant as described herein may have a cover (e.g., cover 22 of implant 10 as shown in FIGS. 1-5) that may be snapped, pressed, or otherwise locked into place on the frame (e.g., frame 12 of implant 10) at a desired point in the installation process. For example, frame 12 may be fastened to a plurality of bone anchors without the cover 22 in place in order to provide more free space for the surgeon to work (e.g., on bone or tissue that would otherwise be covered by cover 22), and then cover 22 may be installed onto frame 12 after such work is completed. For example, as shown in FIG. 1A, cover 22 may have one or more edges, ridges, nubs, or other protrusions 15, 17 configured to be snapped into corresponding grooves or other recesses 25, 27 formed in transverse portions 18, 20 of frame 12. Alternatively or additionally, transverse portions 18, 20 of frame 12 may have one or more edges, ridges, nubs, or other protrusions configured to be snapped into corresponding grooves or other recesses formed in cover 22. The covers and frames of the other implants described herein may have similar arrangements.

Using an implant 10, 50, or 80 as described above, a spine 30 may be repaired after resection of posterior elements of the spine by installing a plurality of bone screws 40 or other bone anchors in the spine 30, each of the plurality of bone screws 40 or other bone anchors having a head 32 and a cap 34 threadably engageable with the head 32, and positioning an implant 10, 50, or 80 such that attachment portions (e.g., 14, 16 of implant 10; 54, 56 of implant 50; or 84, 86, 88, 92, 94, 96 of implant 80) of a frame (e.g., 12, 52, 82) of the implant are respectively disposed in the heads 32 of the bone screws 40 or other bone anchors. The implant 10, 50, or 80 may be secured to the spine by fastening the threaded caps 34 to the respective heads 32 of the bone screws 40 or other bone anchors such that the attachment portions of the frame are captured between each respective cap 34 and head 32, wherein at least one cover (e.g., 22, 62, 102) extending between at least two portions of the frame is configured for protecting a portion of the spine 30, and each of a plurality of spaces (e.g., 26, 66, 106) between the at least one cover and the frame is configured to accommodate the head 32 of one of the bone screws 40 or other bone anchors. In the case of implant 50, additional bone screws 40 or other bone anchors and/or an occipital plate with anchoring heads may be installed in the occipital region of the skull 35, and extensions 68, 70 may be fastened between the heads 32 and threaded caps 34 of such additional bone screws 40 or other bone anchors. If the implant is not already contoured, the method of repair may include shaping the implant (e.g., the frame and/or cover) to a desired contour. As described above, in lieu of or in addition to threaded caps 34, in some embodiments the attachment portions (e.g., rod portions) of the frame and/or the extensions 68, 70 may be secured to the bone anchor heads using clamps, pins, crimps, interlocking shapes, or any other suitable securing mechanism.

Using an implant 120 as described above, a spine 30 may be repaired after resection of posterior elements of the spine by installing a plurality of bone screws 40 or other bone anchors in the spine 30, each of the plurality of bone screws 40 or other bone anchors having a head 32 and a cap 34 threadably engageable with the head 32; installing a plurality of rods (e.g., 144, 146) in the heads 32 of the bone screws 40 or other bone anchors; fastening the plurality of rods to the heads 32 of the bone screws 40 or other bone anchors using the threaded caps 34; and fastening the implant 120 to the plurality of rods using a plurality of set screws 122; wherein at least one cover (e.g., 124, 126) of the implant 120 extending between spaced apart transverse members 112, 142 is configured for protecting a portion of the spine 30; and wherein the transverse members 112, 142 have a plurality of attachments 114 each of which has a recess 116 configured for receiving one of the plurality of rods. In some embodiments, the at least one cover may include a plurality of covers slidably engaged with each other, and the method of repair may include positioning the plurality of covers with respect to each other to achieve a desired length for implant 120, and fixing the position of the plurality of covers with one or more set screws 128. In some embodiments, the attachments 114 may be mounted to shafts 138 that are adjustably disposed in the transverse members 112, 142, and the method of repair may include positioning the shafts 138 with respect to transverse members 112, 142 to achieve a desired width for implant 120, and fixing the position of the shafts 138 with a plurality of set screws 118. If the implant is not already contoured, the method of repair may include shaping the implant (e.g., the transverse members and/or the one or more covers) to a desired contour. As described above, in lieu of or in addition to threaded caps 34, in some embodiments the rods may be secured to the bone anchor heads using clamps, pins, crimps, interlocking shapes, or any other suitable securing mechanism.

Persons of ordinary skill in the art will appreciate that implants as described herein may be used to restore the protective function of the vertebral arches for the spinal dura, maintain adequate clearance between the skin and spinal dura in the event of paraspinal tissue atrophy, eliminate or minimize outwardly visible and unsightly concave defects along the posterior aspect of the spine, prevent adhesion of scar tissue to the dura, and simultaneously stabilize the relative positions of vertebrae to a desired degree.

The embodiments described above are some examples of the current invention. Various modifications and changes of the current invention will be apparent to persons of ordinary skill in the art. Among other things, any feature described for one embodiment may be used in any other embodiment, and methods described and shown in the figures may be combined. Also, words such as "superior," "inferior," "first," "second," "lateral," "medial," "transverse," "axial," "longitudinal," and the like are intended to distinguish among elements and should not be construed to require any particular order, importance, direction, orientation, or other limitation unless the context so requires. In addition, the order of steps shown in the figures and described above may be changed in different embodiments. The scope of the invention is defined by the appended claims, considering the doctrine of equivalents, and is not limited to the specific examples described herein.

What is claimed is:

1. A spinal implant comprising:
   a first transverse member;
   a first cover depending from said first transverse member;
   a second transverse member;
   a second cover depending from said second transverse member;
   said first and second covers being in overlying sliding engagement with one another; and
   a plurality of attachments depending from each of said first and second transverse members, wherein each of said plurality of attachments comprises a recess configured for receiving a mounting rod.

2. The spinal implant of claim 1 wherein each of said plurality of attachments is mounted to a shaft slidably disposed in one of said first and second transverse members.

3. The spinal implant of claim 2 wherein said shaft comprises a ball seated in a respective one of said plurality of attachments.

4. The spinal implant of claim 3 further comprising:
   a first plurality of set screws configured for respectively fixing each of said shafts with respect to one of said first and second transverse members; and
   a second plurality of set screws configured for respectively fixing each of said plurality of attachments with respect to a mounting rod and respectively fixing a rotational position of each of said plurality of attachments with respect to said ball.

5. The spinal implant of claim 1 wherein each of said first and second covers comprises a plurality of fenestrations.

6. The spinal implant of claim 5 wherein said plurality of fenestrations comprises a plurality of elongated slots.

7. A method of repairing a spine comprising:
   installing a plurality of bone anchors in the spine, each of said plurality of bone anchors having a head with a recess;
   installing a plurality of rods in said recesses of said heads of said plurality of bone anchors;
   fastening said plurality of rods to said heads of said plurality of bone anchors; and
   fastening an implant to said plurality of rods using a plurality of set screws;
   wherein said implant comprises at least one cover extending between spaced apart transverse members and configured for protecting a portion of the spine; and
   wherein said transverse members comprise a plurality of attachments each of which comprises a recess in which one of said plurality of rods is disposed.

8. The method of claim 7 wherein said at least one cover comprises a plurality of covers slidably engaged with each other.

9. The method of claim 8 further comprising fixing a position of said plurality of covers with at least one set screw.

10. The method of claim 8 wherein at least two of said plurality of covers are in overlying sliding engagement with one another.

11. The method of claim 10 further comprising positioning said plurality of covers with respect to each other to achieve a desired length for said implant.

12. The method of claim 8 wherein each of said plurality of attachments is mounted to a shaft that is adjustably disposed in one of said transverse members, said method further comprising:
- positioning each said shaft with respect to one of said transverse members to achieve a desired width for said implant; and
- fixing a position of each said shaft with a set screw.

13. The method of claim 8 further comprising shaping said implant to a desired contour.

* * * * *